| United States Patent [19] | [11] Patent Number: 5,004,830 |
| Park et al. | [45] Date of Patent: Apr. 2, 1991 |

[54] PROCESS FOR OXIDATION OF ALKYL AROMATIC COMPOUNDS

[75] Inventors: Chang M. Park; Wayne P. Schammel, both of Naperville, Ill.

[73] Assignee: Amoco Corporation, Chicago, Ill.

[21] Appl. No.: 443,556

[22] Filed: Nov. 29, 1989

[51] Int. Cl.$^5$ ............................................. C07C 51/215
[52] U.S. Cl. ..................... 562/413; 502/171; 502/173; 502/324; 562/416; 562/417; 562/480
[58] Field of Search ............... 562/413, 416, 417, 480; 502/171, 173, 324

[56] References Cited

U.S. PATENT DOCUMENTS

| 3,092,658 | 6/1963 | Baldwin et al. ..................... 562/413 |
| 4,398,040 | 8/1983 | Suzuki et al. ........................ 562/413 |
| 4,755,622 | 7/1988 | Schammel et al. ................. 562/413 |
| 4,764,639 | 8/1988 | Schammel ............................ 562/416 |
| 4,769,487 | 9/1988 | Hundley et al. ..................... 562/413 |
| 4,816,601 | 3/1989 | Lowry et al. ........................ 562/413 |

*Primary Examiner*—Werren B. Lone
*Assistant Examiner*—Vera C. Clarke
*Attorney, Agent, or Firm*—Gunar J. Blumberg; William H. Magidson; Ralph C. Medhurst

[57] ABSTRACT

A process is disclosed for liquid phase oxidation of alkyl aromatic hydrocarbons to aromatic carboxylic acids in presence of a multivalent catalyst promoted by a source of bromine. The oxidation is conducted in at least two oxidation reactions. Exothermic heat of reaction is controlled by means of a liquid phase heat exchanger to control temperature and pressure. Oxygen partial pressure in each stage is at least 1.5 psia to minimize oxygen starvation and improve selectivity. Low reactor temperature, high reactor pressure and improved selectivity improve product yield and product quality.

6 Claims, 1 Drawing Sheet

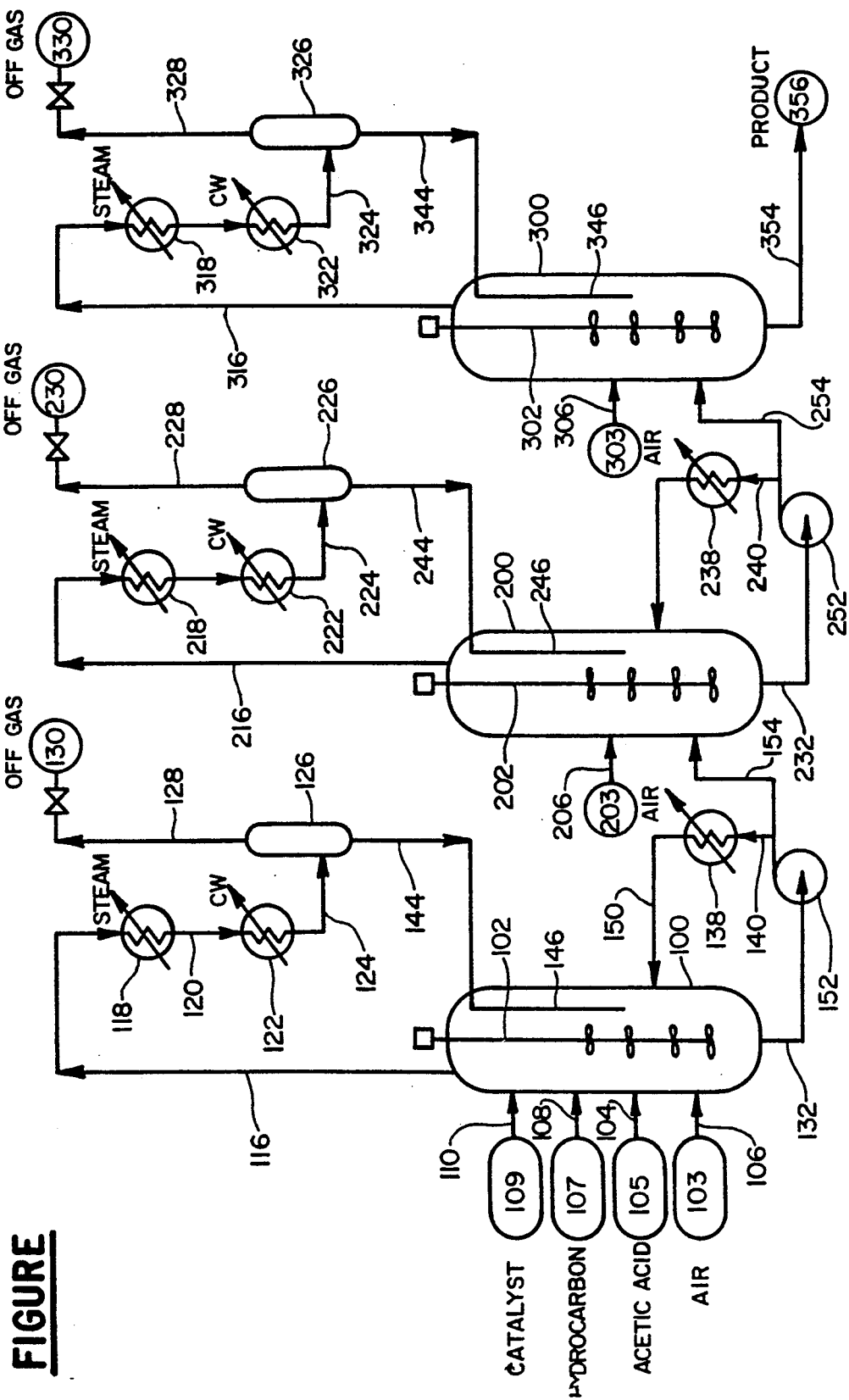
FIGURE

PROCESS FOR OXIDATION OF ALKYL AROMATIC COMPOUNDS

FIELD OF THE INVENTION

This invention relates to liquid phase oxidation of alkyl aromatic hydrocarbons to aromatic carboxylic acids in the presence of a multivalent catalyst promoted by a source of bromine. The oxidation is conducted in at least two stages. Heat generated by the reaction in the first stage is controlled by a liquid phase heat exchanger to control the rate of reaction and thus cause only a partial oxidation of the alkyl aromatic hydrocarbon in the first stage to mono-acids and mono-aldehydes. Partial pressure of oxygen in each stage is at least greater than about 1.5 psia. Oxidation of the alkyl aromatic hydrocarbon to mono-acids and mono-aldehydes is thus maximized and production of by-products is minimized in the first stage. In the second and succeeding stages, the oxidation is continued under controlled conditions to complete oxidation.

BACKGROUND OF THE INVENTION

Highly pure aromatic acids, i.e., benzoic acid, isophthalic acid, phthalic acid, terephthalic acid trimellitic acid, trimesic acid, etc., are of great commercial importance and are widely used for production of various polymers and other materials, including plasticizers and surface coatings. Polyesters are typically prepared from terephthalic acid by direct condensation polymerization with a polyalcohol. High-performance amideimide polymers are prepared by reacting trimellitic acid with an aromatic diamine. Reaction of trimellitic acid with alcohols such as 2-ethylhexanol results in plasticizers such as trioctyltrimellitate.

Preparation of aromatic acids, i.e., benzoic acid, isophthalic acid, terephthalic acid, trimellitic acid, trimesic acid, etc., by oxidation of alkyl aromatic hydrocarbons in two or more stages in the presence of a catalyst composed of cobalt, manganese and bromine is known in the art. For example, trimellitic acid from pseudocumene in a 2-stage liquid phase oxidation is reported in Japanese No. 56,002,932; G.B. No. 1406,693; U.S. Pat. No. 4,398,040; U.S. Pat. No. 4,284,523; Japanese No. 56,128,730; Japanese No. 57,167,942; Japanese No. 57,046,976; Belgium No. 902,545; U.S. Pat. No. 4,587,350; Japanese No. 63,066,149; U.S. Pat. No. 4,755,622; U.S. Pat. No. 4,764,639; and U.S. Pat. No. 4,816,601. Terephthalic acid from a mixture of p-xylene and methyl p-toluate in a multi-stage liquid phase oxidation reaction is reported in U.S. Pat. No. 4,269,805.

Despite the use of multi-stage oxidation processes in the oxidation of alkyl aromatic hydrocarbons as reported in the above prior art, prior investigators failed to recognize that increased oxygen concentration to increase selectivity, coupled with reduced reaction temperatures and increased total pressure would increase product yield and improve product purity. Particularly, prior investigators failed to recognize that increased oxygen concentration and increased total pressure, with lowered solvent partial pressure in the early stages of oxidation of alkyl aromatic hydrocarbons, significantly reduced the production of product impurities, particularly high-boiling impurities which are difficult to remove in downstream purification steps.

Aromatic polycarboxylic acids are conventionally producted by liquid phase catalytic oxidation of feedstocks containing a polyalkyl substituted aromatic hydrocarbon, such as xylene. Such liquid phase reaction systems are shown in U.S. Pat. Nos. 3,170,768 and 3,092,658, both to Baldwin. Because the chemical conversion of the polyalkyl substituted aromatic reactant to the aromatic polycarboxylic acid product is exothermic, reaction solvents are typically employed to dissipate the resultant heat of reaction in a reflux loop. The current practice is to produce the aromatic polycarboxylic acid product in a continuous process or system that includes an oxidation reactor equipped with a reflux system. The reactor contents include water, dior trimethyl substituted hydrocarbon reactants, reaction solvent, and a suitable oxidation catalyst for effecting conversion of the reactants to the desired polycarboxylic acid product. The oxidation reactor is also equipped with means of agitating the reactor contents.

In a conventional continuous oxidation process for producing aromatic carboxylic acids from an alkyl aromatic wherein the catalyst is a composition of cobalt, manganese and bromine, and the solvent is a mixture of acetic acid and water, excess heat from the exothermic reaction is removed by utilizing the vaporization of the reaction solvent. Under typical conditions of the reaction, despite a total reaction pressure of several hundred pounds per square inch, oxygen partial pressure can be at a relatively low level because the bulk of the system vapor pressure is caused by the solvent vapor pressure, i.e., of the water and acetic acid. The solvent vaporization typically takes place in the oxidation reactor, and condensation of the vapors emanating from the reaction mixture typically takes place in a series of heat exchangers. The heat exchangers typically physically located above the oxidation reactor allow condensed solvent vapors to be refluxed to the oxidation reactor by gravity.

Removal of the heat of the reaction by solvent vaporization, and subsequent condensation in heat exchangers, to control reaction temperature results in reduction of the partial pressure of oxygen and consequent production of by-product impurities due to a limited supply of oxygen. For example, p-xylene in the presence of a cobalt, manganese and bromine catalyst can be oxidized to compounds such as trimethyl diphenylmethane in the presence of a limited supply of oxygen.

Other methods than using the vaporization of the reaction solvent for removing the excess heat of reaction, and thereby controlling the reaction temperature, have been disclosed in the prior art. For example, Belgian Pat. No. 741,534 teaches use of a heat exchanger wherein the chemical compound to be oxidized is first passed into a reaction zone, then withdrawn into a heat exchanger wherein air is injected. The reaction mixture is then returned from the heat exchanger to the reaction zone after removal of excess heat from the reaction mixture. Efficiency of the heat exchanger is maintained by the injection of air into the heat exchanger to reduce fouling of the reactor and heat exchanger.

U.S. Pat. No. 4,269,805 teaches a multi-stage reactor for oxidation of alkyl aromatics, e.g., a mixture of p-xylene and methyl toluate in a liquid phase reaction mixture with oxygen-containing gases, e.g., air, under pressure and temperature in the presence of oxidation catalyst. An internally disposed cooling conduit system containing a coolant for removing the heat of reaction is provided and includes a group of cooling conduits for each of the reaction chambers. Temperature of the first stage is maintained generally at about 150°–155° C.

(302-311° F.) and the temperature in successive stages is increased in increments of about 5°-10° C. Pressures of 3 to 10 bar (45 to 150 psi) are taught for oxidation of p-xylene. The reactor is an elongated horizontal closed tank with multiplicity of neighboring reaction chambers arranged successively from one end to the other end of the tank for containing the liquid reaction mixture at predetermined levels in each chamber. The several reaction chambers in the reactor are under the same pressure which is relatively low.

Many prior art oxidation reactors were originally designed to operate at a predetermined temperature range. For a variety of reasons, including product quality, it is desirable to reduce the reaction temperature to below the temperature ranges previously utilized for the oxidation reaction.

Reduced reaction temperatures tend to reduce undesirable burning losses of the polyalkyl aromatic reactant as well as the solvent. Reduced reaction temperatures have been observed to result in a reduction of undesirable oxidation reaction by-products. Thus, it is desirable to reduce the process temperature range so as to improve product yields and quality while reducing process operating costs.

In the conventional polyalkyl aromatic oxidation process, lower reaction temperatures require a simultaneous reduction in the reactor operating pressure. However, as the reactor pressure is reduced, vapor velocities in the reactor increase with attendant reduction in reactor liquid phase residence times. Pressure drops in overhead piping and heat exchangers increase as well. Consequently, as the reactor temperatures are lower in a conventional polyalkyl aromatic oxidation process, equipment limitations are encountered which require either a reduction in unit throughput or significant capital expenditures for equipment alterations needed to maintain capacity.

As the system total pressure is reduced in a conventional process to achieve the desired lower temperature, the oxygen partial pressure at a given dry basis vent oxygen content is also reduced, which decreases selectivity. Accordingly, it is desirable to provide an improved alkyl aromatic oxidation process that can be operated at relatively low oxidation temperatures and at a relatively high pressure wherein oxygen partial pressure is sufficient to increase selectivity. It is therefore an object of this invention to provide a process for the preparation of aromatic mono- or polycarboxylic acids by oxidation of alkyl aromatic hydrocarbons in the presence of a cobalt-manganese-bromine catalyst in an acetic acid-water solvent wherein formation of by-products and impurities is suppressed by use of high reactor pressures and relatively low process temperatures, and wherein oxygen starvation in the reactor is minimized with consequent improved selectivity and improved product yield.

It is further an object of this invention to provide a batch, a semi-continuous or a continuous process for the preparation of aromatic mono- or polycarboxylic acids by oxidation of alkyl-aromatic hydrocarbons in an acetic acid-water solvent solution in the presence of a cobalt-manganese-bromine catalyst wherein formation of by-products and impurities is suppressed in at least a two-stage oxidation reaction wherein selectivity to mono-acids and mono-aldehydes in the first stage is increased by maintenance of oxygen partial pressure. In the second stage and succeeding stages, the oxidation reaction is continued to complete oxidation. The instant invented process is particularly directed to preparation of aromatic polycarboxylic acids such as terephthalic acid, trimellitic acid, and pyromellitic acid from paraxylene, pseudocumene and durene, respectively.

SUMMARY OF THE INVENTION

An improved process is disclosed for oxidation of alkyl aromatic hydrocarbons wherein the alkyl group has from 1 to 5 carbon atoms and the number of alkyl groups is from 2 to 4. The process comprises oxidizing an alkyl aromatic hydrocarbon in an aqueous aliphatic monocarboxylic acid solution using oxygen in the presence of a cobalt-manganese-bromine catalyst wherein the oxidation reaction occurs in at least two stages: the first stage to maximize oxidation of the alkyl aromatic hydrocarbon to mono-acids and/or mono-aldehydes, while suppressing the formation of by-product impurities; the second stage, and succeeding stages, to maximize oxidation of said mono-acids and/or mono-aldehydes to polycarboxylic acid compounds. Heat generated by the reaction is controlled by a liquid phase internal or external heat exchanger, or by removal of product and condensation of vapor. Solvent vaporization is suppressed. Reaction oxygen partial pressure minimizes oxygen starvation and improves selectivity. Formation of by-products and impurities is suppressed to improve product yield and product quality.

FIGURE

The FIGURE is a schematic representation of the novel process for oxidation of alkyl aromatic compounds.

DETAILS OF THE INVENTION

The instant invented process for oxidation in an acetic acid-water solution of alkyl aromatic hydrocarbons to aromatic polycarboxylic compounds is applicable to any alkyl aromatic wherein the catalyst is a cobalt-manganese-bromine catalyst and oxygen is present. Accordingly, the instant invented process can be used for oxidizing any alkyl aromatic wherein the desired product is a polycarboxylic acid compound. Such alkyl aromatic hydrocarbons include metaxylene, orthoxylene, paraxylene, pseudocumene, mesitylene, durene, and compounds such as

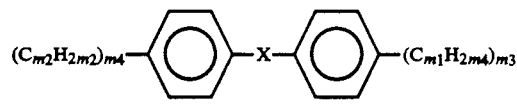

wherein $n_1$ and $n_2$ are whole integers of 1 to 5, $n_3$ and $n_4$ are whole integers of 1 to 2, and —X— is selected from the group consisting of —O—, —$SO_2$, —$CO_2$— and polyalkyl naphthalenes. In preferred embodiments of the method of this invention, paraxylene is oxidized to terephthalic acid and pseudocumene is oxidized to trimellitic acid. The invented process can be either in batch, semicontinuous or continuous method.

The instant process comprises increasing reaction oxygen partial pressure in the first stage by reducing solvent vaporization through liquid phase heat exchange. Reaction pressure, being comprised of the partial pressures of all the vapor constituents, is principally the result of the partial pressures of the water and acetic acid present as the solvent. Reduction of solvent vaporization is accomplished by withdrawing a portion of the solvent liquid from the first stage, removing heat from the withdrawn liquid by means of a liquid phase heat exchanger, and returning the cooled solvent liquid to the first reactor stage to reduce the vapor partial pressure within the reactor. In the event the oxidation reaction products in the solvent liquid are limited in solubility in the liquid, the heat exchanger is preferably a non-foulling type, such as a scraped surface exchanger.

Saturated solvent vapor from each stage reactor headspace, condensed to produce a two-phase composition, is transferred to a gas-liquid separator. The liquid phase is transferred back into the stage reaction zone. The gaseous portion of the two-phase composition is conveyed to an off-gas site for further processing, as desired. Since the off-gas typically includes residual vapors of reactant and solvent, as well as noncondensible gases, it may be economically advantageous to recover the residual reactant and, solvent vapors before the noncondensible gases are vented.

The first oxidation stage maximizes the oxidation of the alkyl aromatic hydrocarbon to mono-acids and mono-aldehydes while suppressing the formation of by-products and impurities such as trimethyl diphenylmethane in oxidation of p-xylene.

It is essential that reactor oxygen partial pressure in the first stage be high enough to prevent oxygen starvation and prevent the formation of by-products and impurities due to incomplete oxidation of the feed and from other reactions than oxidation. In the oxidation of p-xylene to terephthalic acid or pseudocumene to trimellitic acid, reactor pressure in the first of at least two reactor stages is within the range of from about 150 psig to about 500 psig, reaction temperature is within the range of from about 200° F. to about 350° F. Preferably reactor pressure in the first oxidation reactor in either oxidation is within the range of from about 150 psig to about 300 psig, at a temperature within the range of from about 250° F. to about 325° F., and oxygen partial pressure is at least 1.5 psia.

In the oxidation of p-xylene to terephthalic acid, it is further essential that the second oxidation reactor be at a pressure within the range of from about 200 psig to about 450 psig and a temperature within the range of from about 300° F. to about 450° F. to complete the oxidation of the mono-acid and mono-aldehyde to mono- or polycarboxylic acids from the alkyl aromatic hydrocarbons. Preferably, reaction pressure is from about 250 to about 375 psig and reaction temperature is from about 375° F. to about 425° F. Oxygen partial pressure is at least 1.5 psia.

In the oxidation of pseudocumene to trimellitic acid, it is essential that the second oxidation stage be at a pressure within the range of from about 200 psig to about 400 psig and a reaction temperature within the range of from about 275° to about 375° F. A third oxidation stage can be at a pressure within the range of from about 75 to 400 psig and reaction temperature can be within the range of from about 300 to 450° F. Oxygen partial pressure is at least 1.5 psia in all stages.

Suitable solvents for use in the instant invented process include any aliphatic $C_2$-$C_6$ monocarboxylic acid such as acetic acid, propionic acid, n-butyric acid, iso-butyric acid, n-valeric acid, trimethyl acetic and caproic acid and water and mixtures thereof. Preferably the solvent is a mixture of acetic acid and water. In the first oxidation reactor, the solvent preferably comprises less than 15 percent of water.

Since water is produced by the oxidation reaction, rate of production of water at a steady rate is controlled by the feed stream water concentration and the rates of withdrawal of condensate and vapor from the second reactor and third reactor if a third reactor is used. The withdrawn material is dehydrated and recycled.

The source of molecular oxygen employed in the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0 to to 10 volume percent oxygen (measured on a solvent-free basis), depending upon the reaction temperature and pressure. For example, when each alkyl substituent on the aromatic ring of the polyalkyl aromatic is a methyl group, a feed rate of the amount of from 1.5 to 2.7 moles per methyl group will provide such 0 to 10 volume percent of oxygen (measured on a solvent-free basis) in the gas-vapor mixture in the condenser. Accordingly, reactor vent oxygen as volume percent of dry off gas can be in the range of from about 0 to about 10, preferably about 5 vol.% of vent gas on a dry basis.

The catalyst employed in the method of this invention comprises cobalt, manganese and bromine components, and can additionally comprise accelerators known in the art. The weight ratio of cobalt (calculated as elemental cobalt) in the cobalt component of the catalyst-to-polyalkyl aromatic in the liquid phase oxidation of the method of this invention is in the range of from about 0.2 to about 10 milligram atoms (mga) per gram mole of polyalkyl aromatic. The weight ratio of manganese (calculated as elemental manganese) in the manganese component of the catalyst-to-cobalt (calculated as elemental cobalt) in the cobalt component of the catalyst in the liquid phase oxidation of the method of this invention is in the range of from about 0.2 to about 10 mga per mga of cobalt. The weight ratio of bromine (calculated as elemental bromine) in the bromine component of the catalyst to total cobalt and manganese (calculated as elemental cobalt and elemental manganese) in the cobalt and manganese components of the catalyst in the liquid phase oxidation of the method of this invention is in the range of from about 0.25 to about 1.2 mga per mga of total cobalt and manganese.

Each of the cobalt, manganese and bromine components can be provided in any of the known ionic or combined forms that provide soluble forms of cobalt, manganese and bromine in the solvent in the reactor. For example, when the solvent is an acetic acid medium, cobalt and/or manganese, acetate tetrahydrate, and/or hydrogen bromide can be employed. The 0.25 to 1.2 bromine-to-total cobalt and manganese milligram atom ratio is provided by a suitable source of bromine. Other bromine sources include elemental bromine ($Br_2$), or ionic bromine (for example, NaBr, KBr, $NH_4Br$, etc.), or organic bromides which are known to provide bromide ions at the operating temperature of the oxidation (e.g., bromobenzenes, benzyl-bromide, mono- and di-bromoacetic acid, bromoacetyle bromide, tetrabromoethane, ethylene-di-bromide, etc.). The total bromine in molecular bromine and ionic bromide is used to satisfy the bromine to metals atom ratio of 0.25 to 1.2. The bromide ion released from the organic bromides at the oxidation operating conditions can be readily determined by known analytical means. Tetrabromethane, for example, at temperatures of about 350° F. (170° C.)

to about 440° F. (225° F.) has been found to yield about 3 effective gram atoms of bromine per gram mole.

In operation, the minimum pressure at which the reactor is maintained is that pressure which will maintain a substantial liquid phase of the alkyl aromatic hydrocarbon and the solvent. The alkyl aromatic hydrocarbon and solvent not in the liquid phase because of vaporization can be removed from the reactor as a vapor-gas mixture, condensed and returned to the reactor. When the solvent is an acetic acid-water mixture, suitable reaction gauge pressure in the range of from about 75 psig to about 400 psig, and typically is in the range of from about 150 psig to about 350 psig. The temperature range in the first reactor is from about 200° F. to about 350° F. at a pressure from about 150 psig to about 500 psig. Oxygen partial pressure is at least 1.5 psia. Temperature in a second reactor is in the range of from about 275° F. to about 350° F. at a pressure within the range of from about 200 psig to about 400 psig. Temperature in a third reactor is in the range of from about 300° F. to about 450° F. at a pressure of from about 75 psig to about 350 psig.

Since the present invention is susceptible to embodiment in various forms, a number of processes as well as a number of systems can embody the principles of the present invention. The present disclosure, therefore, is to be considered merely as an exemplification of the present invention disclosed herein, without limitation of the specific embodiment illustrated.

Suitable polymethyl substituted aromatic hydrocarbons useful as reaction feed-mixture components or reactants in the method of the present invention include polymethyl substituted benzenes such as the dimethylbenzenes, i.e., o-xylene, m-xylene, p-xylene, the trimethylbenzenes such as pseudocumene and mesitylene and the tetramethylbenzenes such as durene, and the polyalkyllnaphthalenes such as 2,6-, and 2,7-dimethylnaphthalene. The respective aromatic polycarboxylic acid products of these polymethyl substituted aromatic hydrocarbons are the dicarboxylic acids, orthophthalic acid, isophthalic acid, terephthalic acid, and the benzenetricarboxylic acids, such as trimellitic acid and trimesic acid, and the benzenetetracarboxylic acids such as 2,6- and 2,7-naphthalene dicarboxylic acids. The method of this invention can be used to produce terephthalic acid, isophthalic acid, and trimellitic acid (1,2,4-benzenetricarboxylic acid).

Suitable catalyst systems include a mixture of cobalt, manganese and bromine compounds or complexes, soluble in the particular volatilizable aqueous solvent employed. A preferred catalyst system is a solution prepared from dry cobalt, selected manganese acetates, and water. A preferred catalyst system may also include a promoter such as aqueous hydrogen bromide.

Referring to the FIGURE, there is shown a system which embodies the principles of the process of the present invention which is directed to the continuous oxidation of pseudocumene to trimellitic acid.

Reactor feed ingredients, comprising an oxygenated gas, solvent, and hydrocarbon reactant, are introduced into a pressurizable oxidation reactor 100 equipped with an agitator 102. The oxygen-containing gas, e.g., air, is provided by an air source 103 and introduced into reactor 100 via a conduit 106. The solvent, e.g., aqueous acetic acid, is provided by solvent source 105 and is introduced into reactor via a conduit 104. The reactant to be oxidized, pseudocumene, is provided by a hydrocarbon source 107 and is introduced into reactor 100 via a conduit 108. In certain situations, it may be expedient to combine the solvent and reactant into a single feed stream. The desired oxidation catalyst is provided by a source 109, and is introduced into the reactor via conduit 110.

Reactor 100 is pressurized and defines an agitated reaction zone wherein the solvent, the suitable polymethyl substituted aromatic hydrocarbon, the oxidation catalyst and the oxygen-containing gaseous stream are combined to produce an agitated reaction mixture.

The agitated reaction mixture in pressurized reactor 100 is maintained at a predetermined reaction temperature and pressure for a predetermined residence time to produce a mixture of reactants and reaction products. A vapor phase and a product-containing liquid phase are present in the reaction zone. A liquid phase heat exchanger 138 controls reaction temperatures.

Safety considerations mandate that the oxidation process is operated at vent-gas oxygen concentrations of less than about 5 mole percent (dry basis) to avoid the possibility of an explosive vapor composition in the overhead vapor system. Accordingly, oxygen levels of vent gas preferably are set at about 0 to about 10 mole percent oxygen.

Heat is removed from the product-containing liquid phase in reactor 100 by withdrawing a portion of the liquid phase from reactor 100 and passing such removed portion via a discharge pipe 132 to a transfer pump 152 and via a conduit 140 into steam-generating exchanger 138. Because of the limited solubility of the oxidation reaction products in the liquid stream at the conditions in the steam-generating exchanger, it is preferably a non-fouling type, such as a scraped surface exchanger. A portion of the stream from transfer pump 152 is passed to pressurized reactor 200 via conduit 154.

In accordance with the system depicted in the FIGURE, a portion of the reactor vapor phase, which possesses sensible and latent heat, exits reactor 100 into a reflux loop via conduit 116, and is introduced into a steam-generating hot condenser 118 by conduit 116. Boiler-feed water is preferably utilized to recover at least some of the latent and sensible heat from the vapor phase, thereby partially condensing the vapor phase and producing useful process stream as well.

The now partially-condensed reactor vapor phase is next introduced via a conduit 120 into a water-cooled cold condenser 122, which further removes some of the latent and sensible heat, to produce a two-phase composition that is transferred via a conduit 124 to a gas-liquid separator 126 from wherein the liquid phase of the two-phase composition is transferred, directly via conduit 144, which terminates in a dip tube 146, to the reaction zone of reactor 100.

The gaseous portion of the two-phase composition is conveyed via a valved pipeline 128 to an off-gas site 130 for further processing, as desired. For example, because the off gas typically includes residual vapors of reactant and solvent, as well as non-condensible gases, it may be economically advantageous to recover at least some of the residual reactant and/or solvent vapors before the noncondensible gases are vented.

A portion of the reaction vapor phase from reactor 200 exits reactor 200 into separator 226 by conduit 216.

In the second reactor stage, heat is removed from the product containing liquid phase in reactor 200 by withdrawing a portion of the liquid phase from reactor 200 and passing such removed portion via a discharge pipe 232 to a transfer pump 252 and via a conduit 240 into steam generating exchanger 238. A portion of the stream from transfer pump 252 is passed to equipment for product recovery or to a third reactor. Product recovery from the aqueous stream is by conventional methods. Reactor vapor phase from reactor 200 is introduced into steam generating condensor 218 and water cooled cold condenser 222. Liquid from separator 226 is returned to reactor 200 via conduit 244 which terminates in dip tube 246. The gas phase is conveyed to an off-gas site for processing by conduit 228.

In the third reactor used in preparation of trimellitic acid, temperature and pressure are controlled by condensation of vapor and by the removal of heat from the third reactor by withdrawing a portion of the liquid phase containing product from the said third reactor by conduit 354. Reactor vapor phase from reactor 300 is introduced into steam generating condensor 318 and water cooled cold condensor 322. Liquid from separator 326 is returned to reactor 300 via conduit 344 which terminates in dip tub 346. The gas phase is conveyed to an off-gas site for processing by conduit 328.

Product recovery from the liquid phase can be be conventional methods.

In summary, the instant invention comprises a batch, semicontinuous or continuous liquid phase process in at least two reactors for production of an aromatic polycarboxylic acid by oxidation of an alkyl aromatic hydrocarbon wherein the alkyl group of the alkyl aromatic hydrocarbon contains from 1 to 5 carbon atoms and the number of alkyl groups is from 2 to 4 in the presence of a bromine-cobalt-manganese catalyst, which process comprises:

(a) preparing in a first reactor a liquid reaction mixture containing water, an aliphatic $C_2$-$C_6$ monocarboxylic acid and said alkyl aromatic, wherein water concentration is in the range of from about 0 to about 15 wt.% wherein mole ratio of bromine to cobalt plus manganese of said catalyst is in the range of from about 0.25 to about 1.2, (b) injecting an oxygen-containing gas into said first reactor at a rate of from about 1.5 to about 2.7 moles of oxygen per alkyl group, (c) oxidizing in said first reactor said alkyl aromatic hydrocarbon in an exothermic reaction at a temperature of from about 200° F. to about 350° F. at a reactor pressure of from about 150 psig to about 500 psig, and oxygen partial pressure of at least 1.5 psia, to prepare mono-acids and mono-aldehydes, (d) controlling said temperature and pressure within said ranges by means of a liquid phase heat exchanger wherein a portion of said liquid reaction mixture is removed from said first reactor, cooled in said heat exchanger and returned to said first reactor as a liquid, (e) transferring a portion of first reactor liquid phase to a second oxidation reactor, wherein water concentration is in the range of from about 0 to about 20 wt.%, wherein mole ratio of bromine to cobalt plus manganese of said catalyst is in the range of from about 0.25 to about 1.2, 1, (f) injecting an oxygen-containing gas into said second reactor at a mole ratio of from about 1.5 to about 2.7 moles of oxygen per alkyl group, (g) oxidizing said portion of first reactor liquid phase in said second oxidation reactor and in succeeding oxidation reactors necessary to complete said oxidation of said alkyl aromatic hydrocarbon at a temperature within the range of from about 275° to about 450°, pressure within the range of from about 75 psig to about 450 psig and oxygen partial pressure of at least 1.5 psia wherein temperature and pressure in said second reactor is controlled by means of a liquid phase heat exchanger wherein a portion of the liquid reaction mixture in said second reactor is removed form said second reactor, cooled in said heat exchanger and returned to said second reactor as a liquid.

(h) recovering said aromatic polycarboxylic acid as product.

In more detail, the preferred polyalkyl aromatic is selected from the group consisting of m- and p-xylene, pseudocumene, and polyalkyl naphthalenes. The respective aromatic polycarboxylic acid products are orthophthalic acid, pyromelitic acid, benzophenone di- and tetracarboxylic acids, oxy-bis(benzene mono- and dicarboxylic acids), and isophthalic acid, terephthalic acid, trimellitic acid, and naphthalene dicarboxylic acids. Suitably, the alkyl groups of the polyalkyl aromatics contain from 1 to 5 carbon atoms and preferably are methyl groups.

In a preferred embodiment of the method of this invention, paraxylene is oxidized to terephthalic acid in a two-stage oxidation reaction. In the first oxidation reaction, reactor pressure is in the range of from about 150 psig to 500 psig, preferably from about 150 to about 300 psig, at a temperature within the range of from about 200° to about 350° F., preferably from about 250° to about 325° F. In the second oxidation reaction, reactor pressure is within the range of from about 200 to about 450 psig and temperature is in the range of from about 300° F. to about 450° F. Oxygen partial pressure is at least 1.5 psia in both oxidations.

In a preferred embodiment of this invention, pseudocumene is oxidized to trimellitic acid in an oxidation to mono-acids and mono-aldehydes at a temperature within the range of from about 200° F. to about 350° F., a pressure within the range of from about 150 psig to about 500 psig, preferably a temperature within the range of from about 250° F. to about 325° F., and a pressure within the range of from about 150 psig to about 300 psig, and an oxygen partial pressure of at least 1.5 psia, wherein the mono-acids and mono-aldehydes are oxidized in a second oxidation at a temperature within the range of from about 275° F. to about 375° F. and a pressure within the range of from about 200 psig and 400 psig, and in a third oxidation at a temperature within the range of from about 300° F. to about 450° F. and a pressure within the range of from about 75 psig to about 400 psig. Temperature and pressure are controlled by the removal of heat from the third oxidation reaction by condensation of vapor and by withdrawing a portion of the liquid as product from the third oxidation reactor. Oxygen partial pressure in each oxidation stage is at least 1.5 psia.

The following examples illustrate the process of the invention but are not to be construed as limiting the scope of the invention.

Pilot plant experiments were performed as examples to quantify the effects of removing the heat of reaction to suppress the solvent vaporization and of increasing the oxygen partial pressure. Internal cooling by means of an internal liquid phase heat exchanger was obtained. The reactor was a 2-liter continuous stirred tank reactor having titanium lined inside walls. The reactor was equipped with an overhead condenser for condensation of the solvent and pseudocumene which vaporized in the reactor during the exothermic liquid phase oxidation. The condensate was removed from the reaction.

The data reported in Table I indicate in Example I that a low oxygen partial pressure of approximately 1.0 psia, with a reactor pressure range of up to 350 psig, and a relatively low reaction temperature of up to 380° F. resulted in recoverable by-products of 11.2 mole percent. An increase of oxygen partial pressure in Example II to approximately 2.0 psia, coupled with increased reactor pressure of up to 400 psig, resulted in almost a 3 mole % increase in product yield and a reduction in recoverable by-products of about 2.5 mole % over the results of Example I. A decrease in reaction temperature of to up to 350° F. in Example III, coupled with a reaction pressure of up to 350 psig but with an oxygen pressure of approximately 1.7 psia, resulted in almost a 3 mole % increase in product yield and also a reduction in by-products of 2.5 mole % over the results of Example I. The data in Example IV indicate that a decrease in reaction temperature of to up to 350° F., coupled with a reaction pressure of up to 400 psig, plus an oxygen partial pressure of approximately 2.7 psia resulted in a product yield of 4.3 mole % over the results reported in Example I, and almost 2 mole % over the results reported in Example III wherein reaction temperature was the same as in Example IV, but reaction pressure was less.

The data accordingly indicate that low reaction temperature, coupled with high reaction pressure and an oxygen partial pressure of at least 1.5 psia improves product yield in oxidation of alkyl aromatic hydrocarbons to aromatic carboxylic acids and reduces production of by-products by improving selectivity to desired product.

EXAMPLE I

This example illustrates the results obtained by an oxidation process in a conventional procedure.

The oxidation of pseudocumene was accomplished by bubbling air through a hot (320° F.) mixture of pseudocumene (225g) with 420g of 95% acetic acid in the presence of cobalt and manganese acetates and HBr and zirconium to 320° F. The base case concentration of cobalt was 0.21 wt.%, manganese was 0.06 wt.%, Zr was 0.005 wt.%, all based on pseudocumene. Enough HBr was added to equal a 0.7 to 1.0 molar bromine to metals ratio. 1.55g of 48% HBr in water was added to the initial catalyst mix. In addition, a tailout catalyst was added gradually to the reaction mixture during the oxidation. This catalyst contained manganese (0.01 wt%) and zirconium (0.005%).

The temperature in this example was gradually raised from 290° F. to 380°) F. over 70 minutes of run time. The pressure was raised from 100 to 350 psig over the same time. Oxygen partial pressure (calculated) was approximately 1.0 psia. Oxygen partial pressure was calculated as of 20 minutes into the run, based on molar oxygen percent in the vent gas, estimated condensible gases present, and total reaction pressure. After the oxidation the reactor contents are collected and analyzed. Results are in Table I.

EXAMPLE II

This example was conducted in the same manner as Example I but the pressure range was from 150 to 400 psig, the pressure being controlled with the removal of the reaction heat through an internal cooling coil through which a cooling fluid was circulated. Results are in Table I. Calculated oxygen partial pressure range was approximately 2.0 psia. Increased reaction pressure improved yield by almost 3 mole % over prior art procedure as taught in Example I. By-product impurities were also reduced by the higher pressure than used in Example I.

EXAMPLE III

This run was identical to Example I but the temperature range was 250° F. to 350° F. and pressure was 100 to 350 psig. The reduced temperature and pressure caused an increase in by-product impurities, i.e., intermediates and low boilers, versus the results in Example II but lower than the results in Example I. Results are in Table I. Calculated oxygen partial pressure was approximately 1.7 psia.

EXAMPLE IV

In this example the conditions were identical to Example I but the temperature was decreased to the range from 250° to 350° F. and the pressure increased to a range of 150° F. to 400 psig. Calculated oxygen partial pressure was approximately 2.7 psia. Temperature was controlled by removal of the heat of reaction through an internal heating coil. Results are in Table I. An increase in yield of almost 2 mole % over Examples II and III was obtained with significant reduction in low boiling compounds, high boiling compounds, carbon monoxide, and carbon dioxide.

TABLE I

Effects of Reaction Total Pressure, Reaction Temperature, and Oxygen Partial Pressure On Oxidation of Pseudocumene

| Reaction Conditions | Example I | Example II | Example III | Example IV |
| --- | --- | --- | --- | --- |
| Reaction Temp °F. | 290–380 | 290–380 | 250–350 | 250–350 |
| Reaction Pressure psig | 100–350 | 150–400 | 100–350 | 150–400 |
| Oxygen Partial Pres., psia (calculated) | 1.0 | 2.0 | 1.7 | 2.7 |
| Results Mole % | | | | |
| Trimellitic Acid | 88.8 | 91.3 | 91.3 | 93.1 |
| By Products | | | | |
| Intermediates | 0.8 | 0.8 | 1.3 | 1.1 |
| Low Boilers | 2.1 | 1.9 | 2.2 | 1.4 |
| High Boilers | 1.5 | 1.1 | 0.8 | 0.4 |
| CO + $CO_2$ | 6.8 | 4.9 | 4.4 | 4.0 |
| Total By-Products | 11.2 | 8.7 | 8.7 | 6.9 |

What is claimed is:

1. A batch, semi-continuous or continuous liquid phase process for production of aromatic polycarboxylic acid by oxidation in at least two reactors of an alkyl aromatic hydrocarbon wherein the alkyl group of said alkyl aromatic hydrocarbon contains from 1 to 5 carbon atoms and the number of alkyl groups is from 2 to 4, in the presence of a bromine-cobalt-manganese catalyst, which process comprises:
   (a) preparing in a first reactor a liquid reaction mixture containing water, an aliphatic $C_2$–$C_6$ monocarboxylic acid and said alkyl aromatic hydrocarbon, wherein water concentration is in the range of from about 0 to about 15 wt.%, wherein mole ratio of bromine to cobalt plus manganese of said catalyst is in the range of from about 0.25 to about 1.2,
   (b) injecting an oxygen-containing gas into said first reactor at a rate of from about 1.5 to about 2.7 moles of oxygen per alkyl group,
   (c) oxidizing in said first reactor said alkyl aromatic hydrocarbon in an exothermic reaction at a temperature of from about 200° F. to about 350° F. at a reactor pressure of from about 150 psig to about 500 psig, and oxygen partial pressure is at least 1.5 psia, to prepare mono-acids and mono-aldehydes, (d) controlling said temperature and said pressure within said ranges by means of a liquid phase heat exchanger, wherein a portion of said liquid reaction mixture is removed from said first reactor, cooled in said heat exchanger and returned to said first reactor as a liquid, (e) transferring a portion of first reactor liquid phase to a second oxidation reactor, wherein water concentration is in the range of from about 0 to about 20 wt.%, wherein mole ratio of bromine to cobalt plus manganese of said catalyst is in the range of from about 0.25 to about 1.2, 1

(f) injecting an oxygen-containing gas into said second reactor at a mole ratio of from about 1.5 to about 2.7 moles of oxygen per alkyl group, (g) oxidizing said portion of first reactor liquid phase in said second oxidation reactor and in succeeding oxidation reactors necessary to complete said oxidation of said alkyl aromatic hydrocarbon at a temperature within the range of from about 275° F. to about 450° F. pressure within the range of from about 75 psig. to about 450 psig and oxygen partial pressure of at least 1.5 psia, wherein temperature and pressure in said second reactor are controlled by means of a liquid phase heat exchanger wherein a portion of the reaction mixture in said second reactor is removed from said second reactor, cooled in said heat exchanger, and returned to said second reactor as a liquid, (h) recovering said aromatic polycarboxylic acid as product.

2. The process of claim 1 wherein said alkyl aromatic hydrocarbon is selected from the group consisting of m-xylene, p-xylene, pseudocumene, and polyalkyl naphthalenes.

3. The process of claim 1 wherein said alkyl aromatic hydrocarbon is paraxylene, said aliphatic $C_2$–$C_6$ monocarboxylic acid is acetic acid, temperature in said first reactor is within the range of from about 200° F. to about 350° F., pressure in said first reactor is within the range of from about 150 psig to about 500 psig and wherein temperature in said second reactor is within the range of from about 300° F. to about 450° F. and pressure in said second reactor is in the range of from about 200 psig to about 450 psig.

4. The process of claim 3 where said temperature in said first reactor is within the range of from about 250° F. to about 325° F., pressure in said first reactor is within the range of from about 150 psig to about 300 psig, said temperature in said second reactor is within the range of from about 300° F. to about 450° F., and pressure in said second reactor is within the range of from about 200 psig to about 450 psig.

5. The process of claim 1 wherein said alkyl aromatic hydrocarbon is pseudocumene, said aliphatic $C_2$–$C_6$ monocarboxylic acid is acetic acid, temperature in said first reactor is within the range of from about 200° F. to about 350° F., pressure in said first reactor is within the range of from about 150 psig to about 500 psig, wherein temperature in said second reactor is within the range of from about 275° F. to about 375° F., pressure in said second reactor is within the range of from about 200 psig to about 400 psig, and temperature in a third reactor is within the range of from about 300° F. to about 450° F. and pressure in said third reactor is in the range of from about 75 psig to about 400 psig wherein temperature and pressure are controlled by the removal of heat from said third reactor by condensation of vapor and by withdrawing a portion of the liquid phase as product from said third reactor.

6. The process of claim 5 wherein said temperature in said first reactor is within the range of from about 250° F. to about 325° F., and said pressure in said first reactor is within the range of from about 150 psig to about 300 psig.

* * * * *

UNITED STATES PATENT OFFICE
CERTIFICATE OF CORRECTION

Patent No. 5,004,830      Dated April 2, 1991

Inventor(s) Chang Man-Park and Wayne P. Schammel

It is certified that error appears in the above-identified patent and that said Letters Patent is hereby corrected as shown below:

| Col. | Line | |
|---|---|---|
| 1 | 31 | "amideimide" should read --amide-imide-- |
| 4 | 49 | "(Cm2H2m2)m4...(Cm1H2m4)m3 --should read $--C_{n2}H_{2n2})_{n4}\cdots(C_{n1}H_{2n1})_{n3}--$ |
| 6 | 13 | "0 to to 10" should read --0 to 10-- |
| 10 | 5 | "form" should read --from-- |
| 11 | 51 | "380°)F" should read --380°F-- |

Signed and Sealed this

First Day of September, 1992

Attest:

DOUGLAS B. COMER

*Attesting Officer*      *Acting Commissioner of Patents and Trademarks*